US012144963B2

(12) United States Patent
Singh et al.

(10) Patent No.: US 12,144,963 B2
(45) Date of Patent: Nov. 19, 2024

(54) IMAGE-GUIDED LUMBAR PUNCTURE ASPIRATION AND INJECTOR SYSTEM AND METHOD

(71) Applicant: ALCYONE THERAPEUTICS, INC., Lowell, MA (US)

(72) Inventors: Deep Arjun Singh, Cambridge, MA (US); P J Anand, Lowell, MA (US)

(73) Assignee: ALCYONE THERAPEUTICS, INC., Lowell, MA (US)

( * ) Notice: Subject to any disclaimer, the term of this patent is extended or adjusted under 35 U.S.C. 154(b) by 295 days.

(21) Appl. No.: 16/932,307

(22) Filed: Jul. 17, 2020

(65) Prior Publication Data

US 2021/0016000 A1    Jan. 21, 2021

Related U.S. Application Data

(60) Provisional application No. 62/893,630, filed on Aug. 29, 2019, provisional application No. 62/875,463, filed on Jul. 17, 2019.

(51) Int. Cl.
*A61M 5/172* (2006.01)
*A61B 17/34* (2006.01)
(Continued)

(52) U.S. Cl.
CPC ......... *A61M 5/172* (2013.01); *A61B 17/3403* (2013.01); *A61M 5/19* (2013.01);
(Continued)

(58) Field of Classification Search
CPC ....... A61B 17/3403; A61B 2017/3413; A61M 5/142; A61M 5/16804; A61M 5/3297;
(Continued)

(56) References Cited

U.S. PATENT DOCUMENTS 6,325,808 B1    12/2001    Bernard et al.
7,670,294 B2 *   3/2010    Kisen ............... A61B 17/3403
                                                    600/459
(Continued)

FOREIGN PATENT DOCUMENTS

CN    110022916 A    7/2019
EP    3362125 A1    8/2018
(Continued)

OTHER PUBLICATIONS

International Preliminary Report on Patentability, corresponding to International Application No. PCT/US2020/042257, mailing date Jan. 18, 2022.
(Continued)

*Primary Examiner* — Laura A Bouchelle
(74) *Attorney, Agent, or Firm* — MARSHALL, GERSTEIN & BORUN LLP

(57) ABSTRACT

An image-guided lumbar puncture aspiration and injector system. The system includes an auto-injection device having a housing, at least one syringe having a fluid, a controller, a processor, a memory, and a display. An imaging device is communicatively coupled to the auto-injection device and captures images of a lumbar puncture area of a patient to be displayed on the display of the auto-injection device, helping identify a location for a lumbar puncture procedure. A needle assembly is coupled to the at least one syringe of the auto-injection device. An outer needle is adapted to be inserted into a location of the lumbar puncture area identified by the imaging device, and an inner needle is adapted to be inserted into the dura of the patient. The outer sheath needle protects the inner needle from contaminants. The controller operates the auto-injection device based on a programmed infusion and aspiration profile.

7 Claims, 13 Drawing Sheets

(51) Int. Cl.
*A61M 5/19* (2006.01)
*A61M 5/20* (2006.01)
*A61M 5/32* (2006.01)
*A61M 5/34* (2006.01)
*A61B 90/00* (2016.01)

(52) U.S. Cl.
CPC ............ *A61M 5/20* (2013.01); *A61M 5/3293* (2013.01); *A61M 5/3297* (2013.01); *A61M 5/34* (2013.01); *A61B 2017/3413* (2013.01); *A61B 2090/378* (2016.02); *A61M 2205/3303* (2013.01); *A61M 2205/3331* (2013.01); *A61M 2205/52* (2013.01); *A61M 2205/582* (2013.01); *A61M 2210/1003* (2013.01); *A61M 2230/06* (2013.01); *A61M 2230/42* (2013.01)

(58) Field of Classification Search
CPC . A61M 5/1452; A61M 5/14566; A61M 5/427
See application file for complete search history.

(56) References Cited

U.S. PATENT DOCUMENTS

| | | | |
|---|---|---|---|
| 8,308,741 | B2 | 11/2012 | Hyde et al. |
| 8,545,440 | B2 * | 10/2013 | Patrick ................. A61M 5/1452 604/82 |
| 9,044,542 | B2 | 6/2015 | Patrick et al. |
| 9,682,193 | B2 * | 6/2017 | Anand ................. A61M 5/1723 |
| 10,441,713 | B1 * | 10/2019 | Feldman ............ A61M 5/16804 |
| 2010/0274202 | A1 | 10/2010 | Hyde et al. |
| 2017/0188990 | A1 | 7/2017 | Von Allmen et al. |
| 2019/0143037 | A1 | 5/2019 | Anand et al. |
| 2019/0159753 | A1 * | 5/2019 | Hsu .................... A61B 17/3403 |

FOREIGN PATENT DOCUMENTS

| | | |
|---|---|---|
| JP | 2012-522604 A | 9/2012 |
| WO | WO-2010/115134 A1 | 10/2010 |
| WO | WO-2018/149671 A1 | 8/2018 |

OTHER PUBLICATIONS

International Search Report and Written Opinion, corresponding International application No. PCT/2020/042257, mailing date Oct. 9, 2020.

European Patent Application No. 20841611, Supplementary European Search Report, dated Jul. 12, 2023.

Japanese Patent Application No. 502799/2022, Notice of Reasons for Refusal, mailing date of Apr. 9, 2024.

* cited by examiner

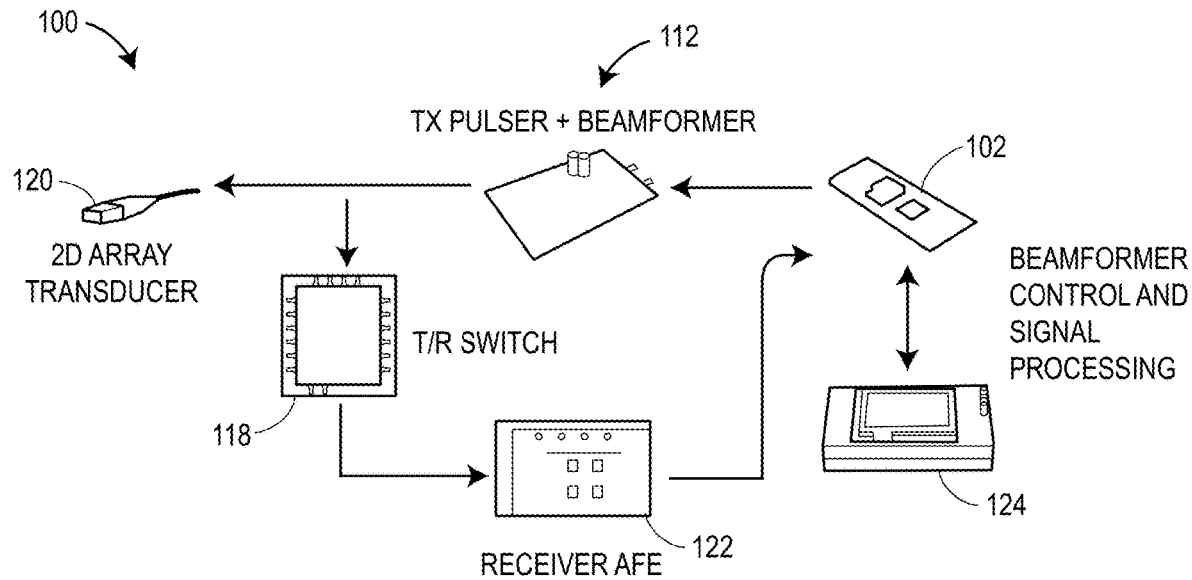

FIG. 15A

| SL NO | UNIT | SPECIFICATIONS | OPTIONS |
|---|---|---|---|
| 1 | Transducer | Type: 2D phased array<br>Elements: 256<br>Active dimension: 16 * 16 | Multiple vendors |
| 2 | TX electronics | Ultrasound Pulser IC EVM<br>Preferred no of channels: 2 | TI TX517<br>or<br>STEVAL-IME009V1<br>or<br>MAX14808 |
| 3 | T/R switch | Transmit/Receive Switch | TI TX810 |
| 4 | RX electronics | Analog Front End EVM | TI AFE5807<br>or<br>AD 9670 |
| 5 | Control and Processing | Single/Combination of DSP based EVMs | TI TMS320C6455 +<br>TI TMS320DM6446<br>or<br>TI TMS320C6678 +<br>TI TMS320DM8148<br>or<br>TI TMS320C6455 +<br>TI TMDSEVM3730 |

FIG. 15B

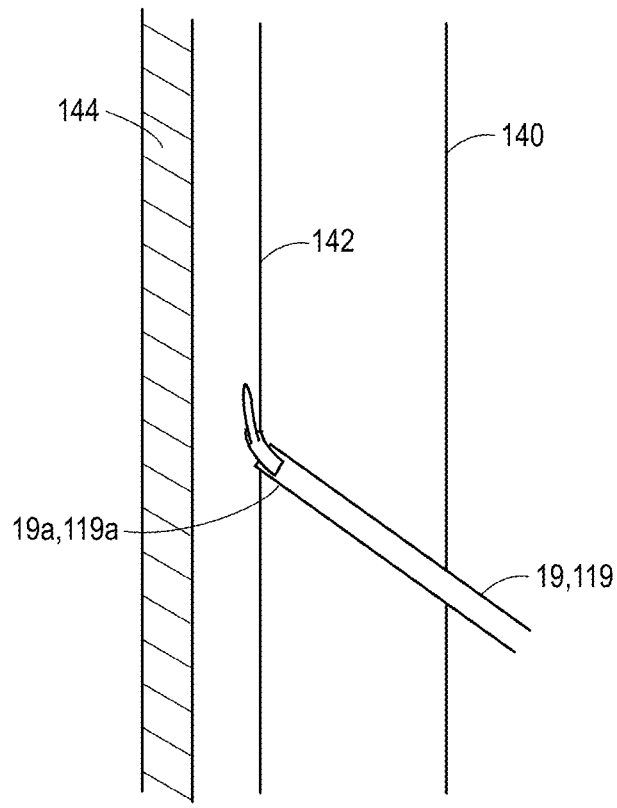
FIG. 19
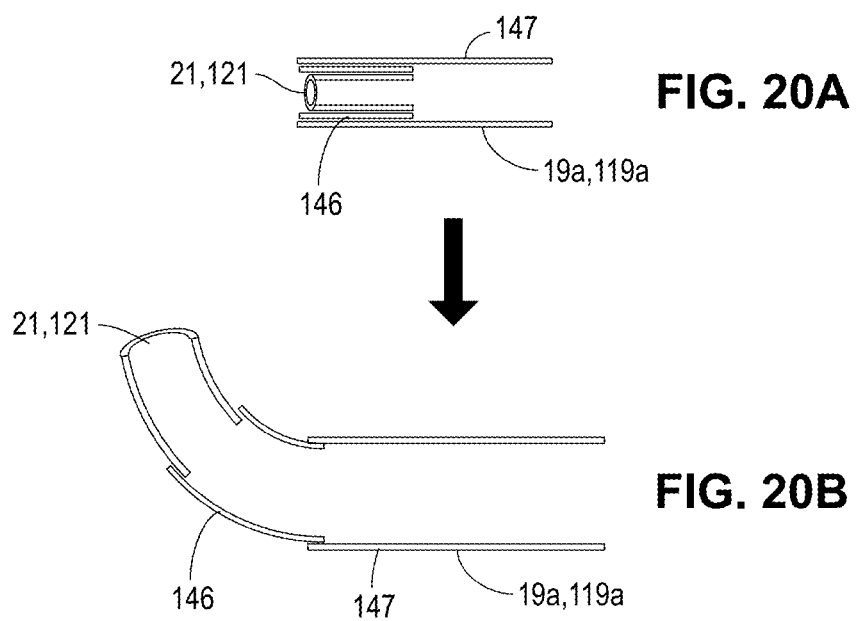
FIG. 20A
FIG. 20B

IMAGE-GUIDED LUMBAR PUNCTURE ASPIRATION AND INJECTOR SYSTEM AND METHOD

CROSS REFERNECE TO RELATED APPLICATIONS

This application claims the benefit of U.S. Provisional Application No. 62/875,463 filed Jul. 17, 2019 and U.S. Provisional Application No. 62/893,630 filed Aug. 29, 2019. The entire content of these applications are incorporated herein by reference in their entireties.

FIELD OF THE DISCLOSURE

The present disclosure generally relates to auto-injection devices and, more particularly, to an image-guided lumbar puncture aspiration and injector system and method.

BACKGROUND

During a lumbar puncture procedure, a local anesthetic is applied to a patient's lower back to numb a puncture site. After the injection site is sufficiently numb, a thin, hollow needle is inserted into the spine of a patient, such as between two lower vertebrae, through the dura and into a spinal canal. The procedure can be used to measure cerebral spinal fluid (CSF) pressure, withdrawn CSF, and/or infuse CSF or other fluids or active molecules.

Delivery of fluids to the intrathecal space is challenging, as the needle (optionally associated with a catheter) is manually inserted into the spine of a patient. Other dangers associated with intrathecal drug administration include infusing a drug too quickly or introducing too much fluid into the space, resulting in a pressure build-up leading to dangerous complications. These considerations are not unique to the intrathecal administration; controlled delivery of material to fluid compartments at other anatomical sites (e.g., an intracerebroventricular site, an intratumoral site) is desired. The training and time required to manually adapt existing drug delivery devices to different anatomical sites and specific treatments represents a significant burden to clinicians.

SUMMARY OF THE DISCLOSURE

According to an aspect of the present disclosure, an image-guided aspiration and injector system comprises an auto-injection device having a housing, at least one syringe carried by the housing and having a fluid, and a controller disposed within the housing. An imaging device is coupled to the auto-injection device and adapted to capture at least one image of a lumbar puncture area of a patient. In addition, a needle assembly is coupled to the at least one syringe of the auto-injection device, and the needle assembly includes an outer needle adapted to be inserted into a location of the lumbar puncture area of the patient identified by the imaging device. An inner needle is disposed within the outer needle and adapted to be inserted into a dura of the patient. The controller is configured to retrieve an infusion and aspiration profile, and the infusion and aspiration profile comprises an infusion and aspiration protocol for the at least one syringe. The controller configured to operate the auto-injection device based on the infusion and aspiration protocol.

According to another aspect of the present disclosure, an image-guided aspiration and injector system comprises an auto-injection device having a housing, at least one syringe carried by the housing and having a fluid, and a controller disposed within the housing. An imaging device is coupled to the auto-injection device and adapted to capture at least one image of a lumbar puncture area of a patient. A needle assembly is coupled to the at least one syringe of the auto-injection device and includes a needle adapted to be inserted into a dura of the patient. A needle guide has a base adapted to be disposed on the lumbar puncture area and a body extending from the base, and the body has an aperture for receiving the needle of the needle assembly. So configured, after the needle is inserted into the aperture of the needle guide and into a location of the lumbar puncture area identified by the imaging device, the controller is configured to retrieve an infusion and aspiration profile. The infusion and aspiration profile comprises an infusion and aspiration protocol for the at least one syringe, and the controller is configured to operate the auto-injection device based on the infusion and aspiration protocol.

According to yet another aspect of the present disclosure, a method for one or more of infusing or aspirating fluid from or into a lumbar puncture area of a patient is disclosed. The method comprises positioning an imaging device one or more of near or into contact with a lumbar puncture area of the patient, and capturing data relative to the lumbar puncture area and processing the data to create at least one image relative to the lumbar puncture area via the imaging device. The method further comprises identifying a location of the lumbar puncture area of the patient for a needle to be inserted via the at least one image generated by the imaging device, and inserting a distal tip of a needle of a needle assembly into the location of the lumbar puncture area, the needle assembly operatively coupled to at least one syringe of the auto-injection device. The method still further comprises activating the auto-injection device to provide a programmed infusion and/or aspiration protocol.

In further accordance with any one or more of the foregoing aspects and methods, one or more of the locking case system, the locking case, and the method of assembling the locking case system may include any one or more of the following forms or method steps.

In one form, the lumbar puncture area may comprise an intrathecal location.

In another form, the image guided aspiration and injector system may further comprise at least one sensor disposed in the auto-injection device and configured to measure at least one pressure associated with the patient. The controller may be configured to operate the auto-injection device based on the infusion and aspiration protocol and the at least one pressure.

In another form, the system may include at least one pressure comprising one or more of an in-line pressure, an infusion pressure, or an aspiration pressure.

In yet another form, the system may further comprise at least one sensor disposed one or more of in or near the lumbar puncture area location, and the at least one sensor is configured to measure at least one physiological parameter for the patient. The controller is configured to operate the auto-injection device based on the infusion and aspiration protocol and the at least one physiological parameter. In addition, the at least one physiological parameter comprises one or more of a cerebrospinal fluid pressure, a cerebrospinal flow rate, an intratumoral pressure, a cerebroventricular pressure, a heart rate, a respiration rate, a protein level, or a biomarker.

In still yet another form, the system may further comprise a display communicatively coupled to the controller, the at least one image to be rendered on the display. The display may be configured to receive an input, and the controller may be configured to operate the auto-injection device based in part on the infusion and aspiration protocol and the received input. In addition, the at least one syringe may include two syringes, at least one of which comprises the fluid.

In another form, the needle assembly may comprise a distal end and a proximal end coupled to the at least one syringe of the auto-injection device. The needle assembly may further comprise a needle having a distal end adapted to change direction, such that an outlet of the distal end is one of rostral facing, distal facing, or directed toward a specific compartmentalized area of a spinal column of the patient. The needle assembly may further include a hub having a tactile sensor disposed therein, the tactile sensor adapted to sense when a dura of the patient is pierced. In addition, the imaging device may comprise an ultrasound transducer employing ultrasound imaging using 2D-phased array transducers, and the ultrasound transducer may comprise an array of transducer elements and any generic array type. Further, the ultrasound transducer may include beam steering scanning that occurs at different angles and images captured during this scanning may be projected onto the display of one or more of the auto-injection device or the remote data station.

In still yet another form, the imaging device may comprise an ultrasound system having one or more of a control and signal processing unit, a transmitter with a transmitter pulser and a transmitter beamformer, a transmit switch, an ultrasound transducer, and a receiver, such that the transmit/receive switch separates the transmitter and the receiver, the ultrasound transducer sends out ultrasound waves, the receiver processes the reflected waves from a target, and a display unit renders the ultrasound images detected. The imaging device may further include at least one imaging sensor and a sensor interface. The at least one imaging sensor may be communicatively coupled to the sensor interface and adapted to capture a profile of a portion of an area in the lumbar puncture area of the patient.

In still other forms, the body of the needle guide may be cone-shaped and extend upwardly from the base of the needle guide. In addition, the body may have a first end including the aperture for receiving the needle and a second end disposed opposite the first end, the second end adjacent to the base. In addition, the base of the needle guide may include an adhesive portion adapted to contact the lumbar puncture area. Further, an entry-point of the needle into the location of the lumbar puncture area may be a center area of one or both of the body of the needle guide or the base of the needle guide, Still further, the needle guide may direct the needle in the center area.

In still yet other forms, the method may comprise applying gel to the lumbar puncture area before positioning an imaging device into contact with the lumbar puncture area. In addition or alternatively, the method may further comprise securing a needle guide to the lumbar puncture area via an adhesive disposed on the needle guide and applying gel to an area of the lumbar puncture area before positioning an imaging device into contact with a lumbar puncture area of the patient, the needle guide protecting the needle from contamination. Further, inserting a distal tip of a needle of a needle assembly into the location of the lumbar puncture area may comprise inserting the distal tip of the needle of the needle assembly first through an aperture of the needle guide and then into the location of the lumbar puncture area. In another example, inserting a distal tip of a needle of a needle assembly may comprise first inserting an outer needle into the location of the lumbar puncture area identified by the imaging device and the inserting an inner needle disposed within the outer needle into a dura of the patient, the outer needle protecting the inner needle from contamination. Still further, activating the auto-injection device to provide a pre-programmed infusion and/or aspiration may comprise selecting a pre-programming infusion and aspiration profile using a display of the auto-injection device, retrieving the selected infusion and aspiration profile from a memory via the controller of the auto-injection device, and carrying out the infusion and aspiration protocol via at least one processor of the auto-injection device.

In still other forms, the method may further comprise displaying the at least one image on a display of one or more of an auto-injection device or a remote data station after capturing data relative to the lumbar puncture area and processing the data to create the at least one image relative to the lumbar puncture area. In addition, activating the auto-injection device to provide a programmed infusion and/or aspiration protocol may comprise controlling the auto-injection device based on both the programmed infusion and/or aspiration protocol and one or more of at least one pressure or at least one physiological parameter associated with the patient and measured by at least one sensor.

BRIEF DESCRIPTION OF THE DRAWINGS

The features of this disclosure which are believed to be novel are set forth with particularity in the appended claims. The present disclosure may be best understood by reference to the following description taken in conjunction with the accompanying drawings, in which like reference numerals identify like elements in the several figures, in which:

FIG. 15A illustrates another exemplary ultrasound system of the present disclosure;

FIG. 15B is a chart depicting exemplary specifications and options for components of the ultrasound system of FIG. 15A;

FIG. 19 is a perspective view of a portion of a needle assembly of the image-guided aspiration and injector system of the present disclosure, the portion of the needle assembly inserted into a lumbar puncture area of a patient;

FIG. 20A is a portion of the needle assembly of the present disclosure in a retracted position; and FIG. 20B is a portion of the needle assembly of FIG. 20A in an extended position.

DETAILED DESCRIPTION

Generally, the system of this disclosure includes an auto-injection device having a pump to control aspiration with pressure monitoring and infusion of fluids at a programmed flow-rate also with pressure monitoring. The system can include one or more sensors for input to control the aspiration and infusion of fluids. For example, a pressure sensor can measure an inline pressure for a lumbar puncture needle and/or tubing and software enabled algorithmic aspiration or infusion flow rates. The auto-injection device also includes an input port having an miniaturized ultrasound transducer or other imaging technologies coupled thereto. This allows a physician to apply gel (if needed for imaging) to a lumbar puncture area and capture images of the lumbar puncture area to accurately identify the correct location for the lumbar puncture procedure, for example. A screen on the auto-injection device housing can be used to display the images captured by the ultrasound transducer.

The gel of the ultrasound procedure can potentially become a contaminant when the needle is inserted into the spinal canal. To avoid this situation, the system herein utilizes a telescoping lumbar puncture needle. In this example, an outer, sheath needle is used to puncture the skin of the patient through the gel coating and the inner, protected needle is then used to be inserted through the dura of the patient.

Alternatively, and in another example, another way to prevent the gel from becoming a contaminant is to have sterile guide (shaped like a small cone with a hole on top) with pre-sterile adhesive base placed onto the needle insertion site on the skin. The gel would be placed after placing the sterile cone, thereby protecting the needle insertion site. The lumbar puncture needle would be placed through the small hole on top of the cone to access the skin and insert the needle.

The system may also include peripheral sensors/electronics that may be used to acquire images of the intrathecal/lumbar space, for example a sensor that is placed on the side(s) or back of the patient to support in image capture. The system can also include software that visualizes the trajectory and target of the needle insertion, to better help with dura targeting and insertion. In addition, the lumbar puncture needle can also be a custom needle with a tactile sensor built into the hub that provides sensing on when the dura is hit and pierced.

Still further, in another example, the lumbar puncture needle may be designed to change direction for an outlet to be rostral (brain) facing or distal facing or towards specific compartmentalized areas in the spinal column like mid-thoracic or cervical.

Figure 1:
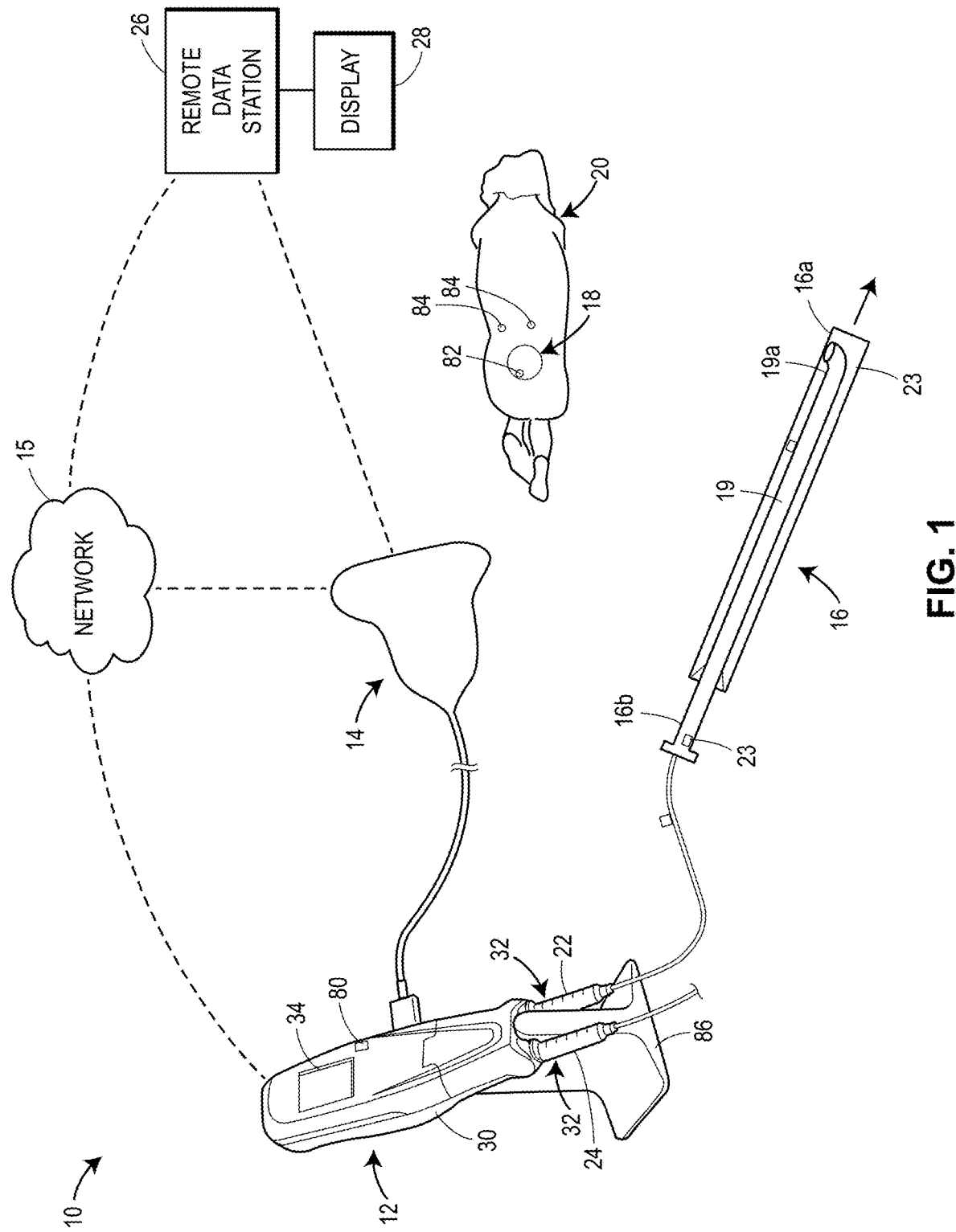
FIG. 1 is an example of an image-guided lumbar puncture aspiration and injector system according to the present disclosure and positioned near a lumbar puncture area of a patient.

Referring now to FIG. 1, an image-guided lumbar puncture aspiration and injector system 10 constructed in accordance with the teachings of the present disclosure is depicted. The image-guided aspiration and injector system 10 includes an auto-injection device 12, an imaging device 14 communicatively coupled to the injector device 12 via a wired connection, and a needle assembly 16 coupled to the auto-injection device 12. The imaging device 14 may be a miniaturized ultrasound transducer or include any other imaging technology. The image-guided aspiration and injection system 10 is positioned in close proximity to a lumbar puncture area 18 of a patient 20 by a clinician. The lumbar puncture area 18 may include an infusion and aspiration location, such as an intrathecal location (e.g., the intrathecal space). In other examples, the infusion and aspiration location may include an intracerebroventricular location or an intratumoral location.

The auto-injection device 12 together with the needle assembly 16 may be used to, for example, deliver a fluid (e.g., a therapeutic agent) 22 to the lumbar puncture area 18 of the patient 20 and/or remove fluid 24 (e.g., cerebrospinal fluid) from the lumbar puncture area 18 of the patient 20. In addition, the imaging device 14 may be used to capture images of the lumbar puncture area 18 to accurately identify a correct location for a lumbar puncture procedure, for example. Such images captured may then be displayed on a screen of the auto-injection device 12 or other display to assist with any infusion and/or aspiration procedure in the lumbar puncture area, for example.

In some examples, the needle assembly 16 includes a distal end 16a adapted to be inserted into the lumbar puncture area 18 of the patient 20 and a proximal end 16b coupled to the at least one syringe 32 of the auto-injection device 12. The needle assembly 16 may further include a telescoping lumbar puncture needle having an outer, sheath needle 17 used to puncture the skin of the patient 20 through the gel coating area and an inner, protected needle 19 used to be inserted through the dura of the patient 20. Such a configuration prevents the gel of the ultrasound procedure from becoming a contaminant when the needle assembly is inserted into the spinal canal of the patient 20.

In some other examples, the inner needle 19 of the needle assembly 16 may include a distal end 19a that is designed to change direction for an outlet 21 to be rostral (brain) facing or distal facing or directed towards specific compartmentalized area in the spinal column, such as mid-thoracic or cervical. In addition, in some examples, the needle 19 of the needle assembly 16 may include a custom needle with a tactile sensor 23 built into a hub that provides sensing on when the dura is hit and pierced. Further, the system 10 may include software that visualizes the trajectory and target of the needle insertion of the needle assembly 16, for example, to better help with dual targeting and insertion.

Alternatively, and as explained more below, a sterile guide having a cone-shaped body with a small aperture on a top portion of the cone-shaped body may be used to prevent the gel from becoming a contaminant. The sterile guide may include an adhesive base placed onto the lumbar puncture area 18, or more generally, the needle insertion site, of the patient 20. The sterile guide is adapted to be placed onto the lumbar puncture area 18 before application of any gel for the ultrasound procedure, thereby protecting the needle insertion site from any contamination. The needle, such as the lumbar puncture needle, is then placed through the small aperture of the sterile guide to access the skin of the patient 20 and inserted into the correct location of the lumbar puncture area 18, which was accurately identified by the imaging device 14 coupled to the auto-injection device 12.

As further depicted in FIG. 1, and in some examples, the image-guided lumbar puncture aspiration and injector system 10 may further include a remote data station 26. The remote data station 26 may be communicatively coupled to one or more of the imaging device 14 and the auto-injection device 12 via one or more of a wired or a wireless connection, such as via the network 15. The remote data station 26 may include a display 28, as explained more below.

In particular, once an accurate location in the lumbar puncture area 18 has been identified via the imaging device 14, the auto-injection device 12 may be activated to deliver the fluid 22 to and/or remove the fluid 24 from the location based on a pre-programmed infusion and aspiration profile. It will be appreciated that the auto-injection device 12 may be pre-programmed with the infusion and aspiration profile off-site, e.g., by someone other than the clinician, or on-site, e.g., by the clinician prior to using the device 12 on the patient 20. As an example, the clinician may enter an infusion and aspiration profile that includes, for example, a volume and a flow rate of the infusion and/or aspiration necessary for the patient 20. In some cases, the auto-injection device 12 may be programmed, off-site, such as via the remote data station 26, with the infusion and aspiration profile and then modified by the clinician and/or modified responsive to at least one pressure and/or at least one physiological parameter associated with the patient 20.

Still referring to FIG. 1, the auto-injection device 12 generally includes a housing 30, at least one syringe 32 carried by (e.g., partially disposed within) the housing 30 and adapted to be coupled to the lumbar puncture area 18 of the patient, such as via the needle assembly 16, and a display 34 disposed on the housing 30. The at least one syringe 32 may include two syringes 32, one of which comprises the fluid 22 (e.g., a therapeutic agent) to be delivered and/or injected into the lumbar puncture area 18 and the other of which comprises fluid 24 (e.g., cerebrospinal fluid) to be aspirated from the lumbar puncture area 18, for example.

In this example, the housing 30 has a substantially rectangular shape that is ergonomic and allows the housing 30 to be hand-held. In particular, a majority of the weight of the auto-injection device 12 may be concentrated toward a proximal end of the housing 30, which allows the auto-injection device 12 to sit comfortably within the palm of the clinician 22 or the patient 18. In this example, the at least one syringe 32 is disposed at a distal end of the housing 30 and the display 34 is disposed at a proximal end of the housing 30. However, in other examples, the display 34 can be disposed at the distal end and the at least one syringe 32 can be disposed at the proximal end. The display 34 may be a touch screen that facilitates interaction with the patient 18 and the clinician 22 through a user interface ("UI"). In particular, the UI may display the operational status of the auto-injection device 10 (e.g., on, off, infusing, aspirating, infusing and aspirating) as well as receive input from the patient 20 and/or the clinician. The UI may, for example, allow the clinician to start, stop, pause, or continue operation of the device 10. The UI may also allow the clinician to pre-program the device 10 prior to use of the device 10 as well as receive other input from the clinician, such as, for example, modifications to the infusion and aspiration profile during operation of the device 12. Additionally, the UI may display various physiological parameters and pressures monitored by the device 12 and images from the imaging device 14, such as ultrasound images.

Figure 2:
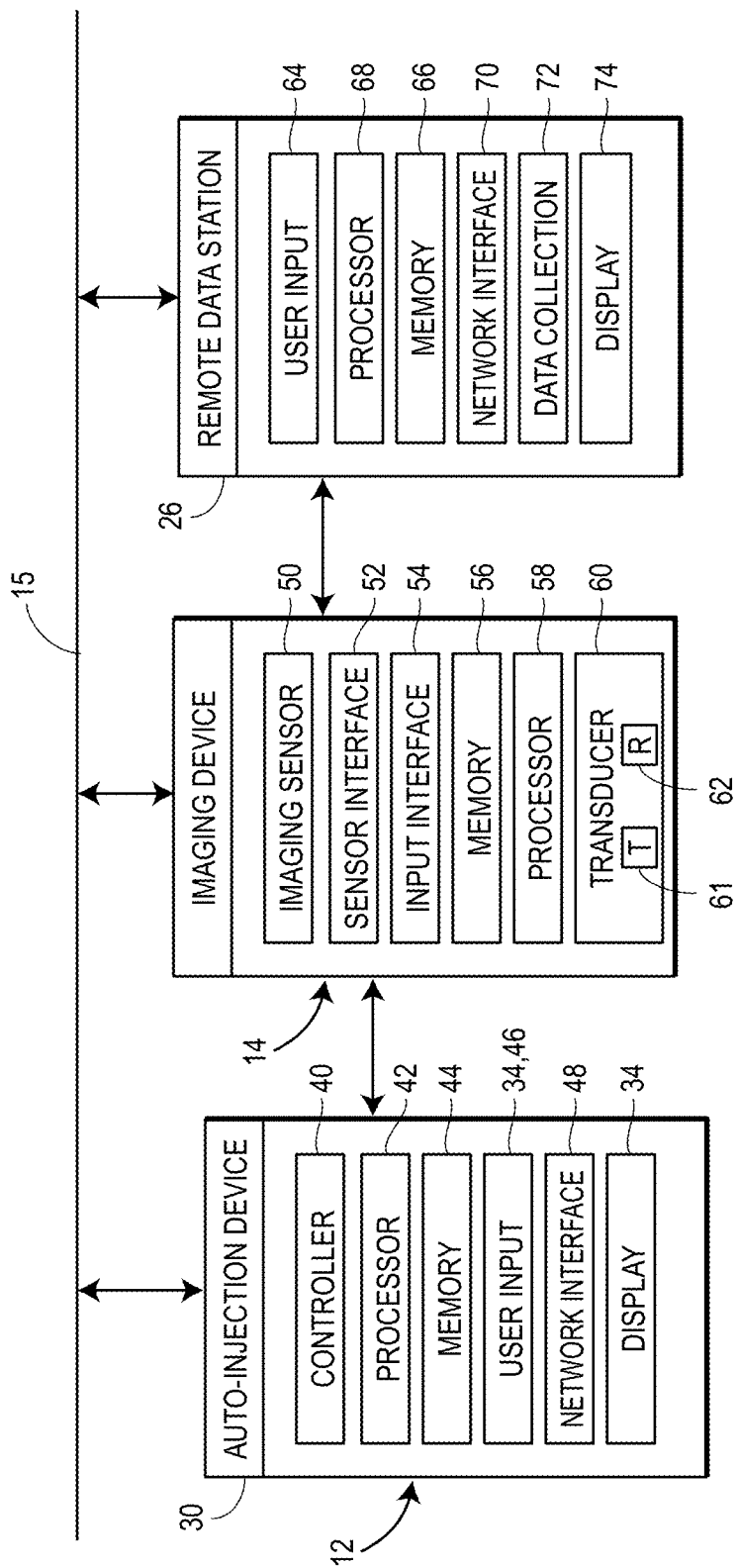
FIG. 2 illustrates a block diagram of the image-guided lumbar puncture aspiration and injector system of FIG. 1.

Referring now to FIG. 2, the auto-injection device 12 also includes a controller 40 disposed in the housing 30. The controller 40 is communicatively coupled to one or more actuators (not shown), which control movement of parts within the auto-injection device 12 to infuse the fluid 24 to the lumbar puncture location 18 and/or aspirate the fluid 24 from the lumbar puncture location 18. The controller 40 and/or the auto-injection device 12 includes one or more processors 42 that implement an infusion and aspiration profile stored in a memory 44 of the auto-injection device 12, such as in the memory of the controller 40. The infusion and aspiration profile that may be stored in the memory 44 includes an infusion and aspiration protocol for at least one of the syringes 34 coupled to the needle assembly 16. Generally, the processor 42 executes the infusion and aspiration protocol. The auto-injection device 12 may also include a user-input 46, which may be the UI of the display 34 of the device 12 and a network interface 48, which allows the auto-injection device 12 to be communicatively coupled to the wireless network 15, for example.

In addition, and generally, the imaging device 14 communicatively coupled to the auto-injection device 12 includes at least one imaging sensor 50, a sensor interface 52, an input interface 54, a memory 56 executable by a processor 58 and a transducer 60. The transducer 60 includes a transmitter 61 and a receiver 62, as explained more below relative to further exemplary imaging devices.

Likewise, and still referring to FIG. 2, the remote data station 26 is communicatively coupled to one or more of the imaging device 14 and/or the auto-injection device 12 via the wireless network 15, for example, also includes a user input 64, a memory 66 executable by a processor 68, a network interface 70, a data collection module 72, and a display 74, which may include or be separate from the user input 64, for example.

Each of the processors 42, 58, and 68 may be a general processor, a digital signal processor, ASIC, field programmable gate array, graphics processing unit, analog circuit, digital circuit, or any other known or later developed processor. The processor 42 of the auto-injection device 12 may operate pursuant to the infusion and aspiration profile stored in the memory 44 of the auto-injection device 12 or the memory 66 of the remote data station 26, for example. The memory 44, 56, 66 may be a volatile memory or a non-volatile memory. The memory 44, 56, 66 may include one or more of a read-only memory ("ROM"), random-access memory ("RAM"), a flash memory, an electronic erasable program read-only memory ("EEPROM"), or other type of memory. The memory 44, 58, 68 may include an optical, magnetic (hard drive), or any other form of data storage.

In one example, the infusion and aspiration protocol is part of the infusion and aspiration profile stored on the memory 44 and includes a set of executable instructions that controls at least one of the syringes 32 to facilitate infusion and/or aspiration of the fluid 22, 24 into the patient 20 using the device 12. The infusion and aspiration protocol may be stored on the memory 44 as computing logic, which includes one or more infusion and aspiration routines and/or sub-routines, embodied as computer-readable instructions stored on the memory 44. The controller 40, particularly the processor 42 thereof, can execute the logic to cause the processor 42 to retrieve the infusion and aspiration profile and control the auto-injection device 12 in accordance with the infusion and aspiration profile. In particular, the infusion and aspiration protocol may specify, among other parameters, whether each of the syringes 32 is to infuse the fluid 22 into the lumbar puncture location 18 or aspirate the fluid from the lumbar puncture location 18, the timing of infusion and/or aspiration, a volume of the fluid to be infused, the flow rate for infusing the fluid, a volume of the fluid to be aspirated, and the flow rate for aspirating the fluid.

Additionally, other data, such as at least one physiological parameter and at least one pressure associated with the patient 20, may be stored in the memory 44. The at least one physiological parameter and the at least one pressure may be previously obtained values (e.g., values measured during a previous use of the device 12, values input into the UI via the clinician, values received via a wired or wireless communication protocol) or values measured during the use of the device 12, either directly by the device 12 or by another device associated with the device 12 and received using a wired or wireless communication protocol. In particular, the at least one physiological parameter may include parameters associated with the infusion and aspiration location 18 or other parameters for the patient 20, such as, for example, a cerebrospinal fluid pressure, a cerebrospinal flow rate, an intratumoral pressure, a cerebroventricular pressure, a heart rate, a respiration rate, a protein level, a biomarker presence, absence, or level, respiration per minute ("RPM"), respiratory diaphragm movements, electrical inputs for patient electrocardiography, or combinations thereof. The at least one pressure may include, for example, an in-line pressure, an infusion pressure, an aspiration pressure, arterial/venous pressure, force limits for different syringe types, other pressure values, or combinations thereof. Additionally, the other data may include various functional variables such as, for example, fluid volumes, number of infusion and aspiration cycles, and time delay between cycles.

Referring back to FIG. 1, the system 10 may also be associated with one or more sensors that measure one or more of these parameters. In some cases, the auto-injection device 12 may include at least one sensor 80 disposed on and/or in the housing 30 that measures one or more of these parameters. In one example, the device 12 may include a pressure sensor that measures the in-line pressure for the lumbar puncture needle and/or tubing, for example. Alternatively or additionally, at least one sensor 82 may be disposed in lumbar puncture area 18 that measures one or more of these parameters. In addition, the at least one sensor 82 and other peripheral sensors/electronics can be used to acquire images of the intrathecal/lumbar space, such as sensors placed on the side or back of the patient 20, to support image capture, for example. The one or more sensors 82 in turn electronically communicate with the controller 40 of the auto-injection device 12, for example, using any known electronic communication methods. For example, the controller 40 may be communicatively connected to the one or more sensors 80, 82 using a hardwired communication scheme as described in detail above, using one or more known wireless communication protocols, or a combination thereof.

In some other examples, the system 10 may be communicatively coupled to at least one sensor 84 disposed on or in the patient 20 at a location other than the lumbar puncture area 18. In some examples, the at least one sensor 84 may be disposed in various locations on the body of the patient 20 to measure various physiological parameters. For example, the at least one sensor 84 could include a body position sensor, which detects changes in the position of the patient 20, a temperature sensor, which detects the overall temperature of the patient 20 or the temperature of a specific part of the body of the patient 18, an electromyography ("EMG") sensor, which measures muscle response or electrical activity of the patient 20, an electrocardiogram ("ECG" or "EKG") sensor, which measures the electrical activity of the heart of the patient 20, an airflow sensor, a galvanic skin response ("GSR") sensor, which measures the electrical conductance of the skin of the patient 20, or combinations thereof. While these sensors have been discussed as being placed on the patient 20, the at least one sensor 84 may also be placed in an article of clothing (e.g., a vest, etc.) worn by the patient 20.

Still further, in other examples, the system 10 may be communicatively coupled to near field communication stickers and/or tags. The near field communication stickers (NFC) and/or tags may be placed on any part of the auto-injection device 12, the imaging device 14, or inside or outside of a body of the patient 20, for example, and other part of the system 10. Such NFC stickers and/or tags may help automate the collection and storage of identification data associated with the patient 20, for example, making any methods associated with the system 10 very patient specific.

In some cases, the infusion and aspiration profile may be stored on a memory outside of the auto-injection device 12 and transmitted to the device 12 prior to usage of the device 12. For example, the infusion and aspiration profile can be stored on the memory 66 of the remote data station 26 (FIG. 2), which may be a desktop computer communicating with the device 12 wirelessly or through a hardwired connection using any of the wireless communication or hardwired communication protocols discussed above. In other examples, the memory 66 of the remote data station 26, such as a remote computing device, may be a mobile electronic device, a smart phone, or a server located away from the device 12. Additionally, the infusion and aspiration profile may be stored on an external memory and transferred to the memory 44 of the device 12 through a hardwired connection. For example, the infusion and aspiration profile can be stored on an external hard drive, a solid-state drive ("SSD"), a portable digital storage device, the Cloud, a Personal Cloud, or a USB Flash Drive, and then transferred to the memory 44, for example. The device 12 may also be communicatively coupled to an external computing device that could, for example, compare the measured at least one physiological parameter and/or at least one pressure to a threshold physiological parameter and/or pressure to determine if the measured at least one physiological parameter and/or at least one pressure is within an acceptable, threshold range. For example, the external computing device could be a desktop computer, a tablet, a mobile phone, server, etc.

Optionally, the device 10 may also be equipped with one or more accessories to facilitate storage, transportation, and/or positioning of the device 10. For example, the device 10 may be equipped with a stand 86, as depicted in FIG. 1.

Figure 3:
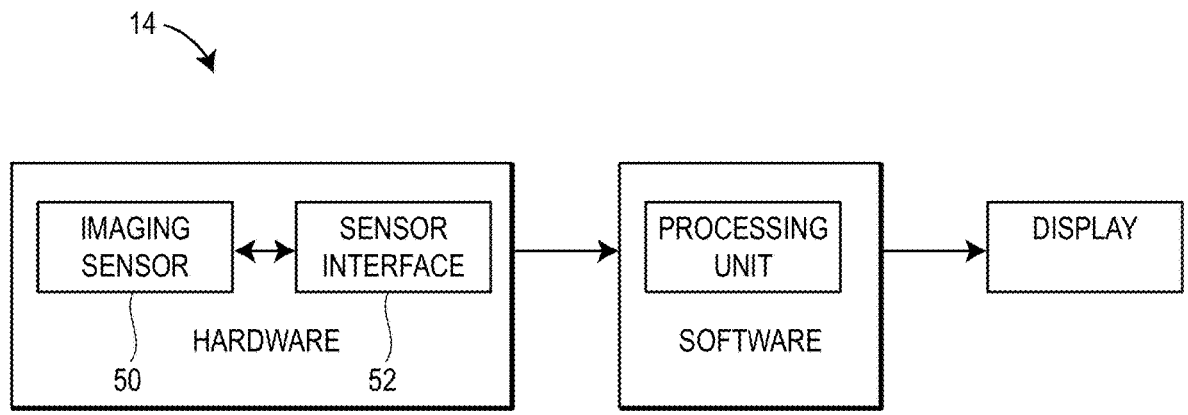
FIG. 3 is a block diagram of a portion of the system of FIG. 1.

Referring now to FIG. 3, a block diagram of a portion of the image-guided aspiration and injector system 10 of FIG. 1 of the present disclosure is depicted. In particular, the imaging sensor 50 is depicted communicatively coupled to the sensor interface 52 of the imaging device 14. The imaging device 14 may capture a 2D profile of a portion of a spinal cord (and an area around the spinal cord) in the lumbar puncture area 18 of the patient 20 (FIG. 1). Analog and digital electronics, including the processing units described above relative to one or more of the auto-injection device 12, the imaging device 14, and/or the remote data station 26, drive, control, and perform signal processing for sensors, such as the imaging sensor 50 of the imaging device 14. Software for processing the acquired data, such as data acquired by the imaging device 14, and creating a 2D image is included. The data, including the 2D images may be included on the display 34 of the auto-injection device 12 or the display 74 of the remote data station 26, for example.

Figure 4:
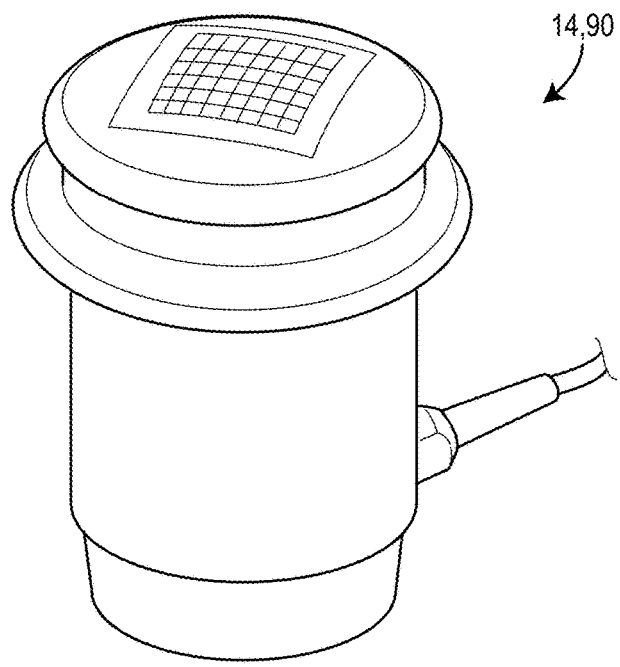
FIG. 4 is an exemplary imaging device, including a transducer, of the system of FIG. 1.
Figure 5:
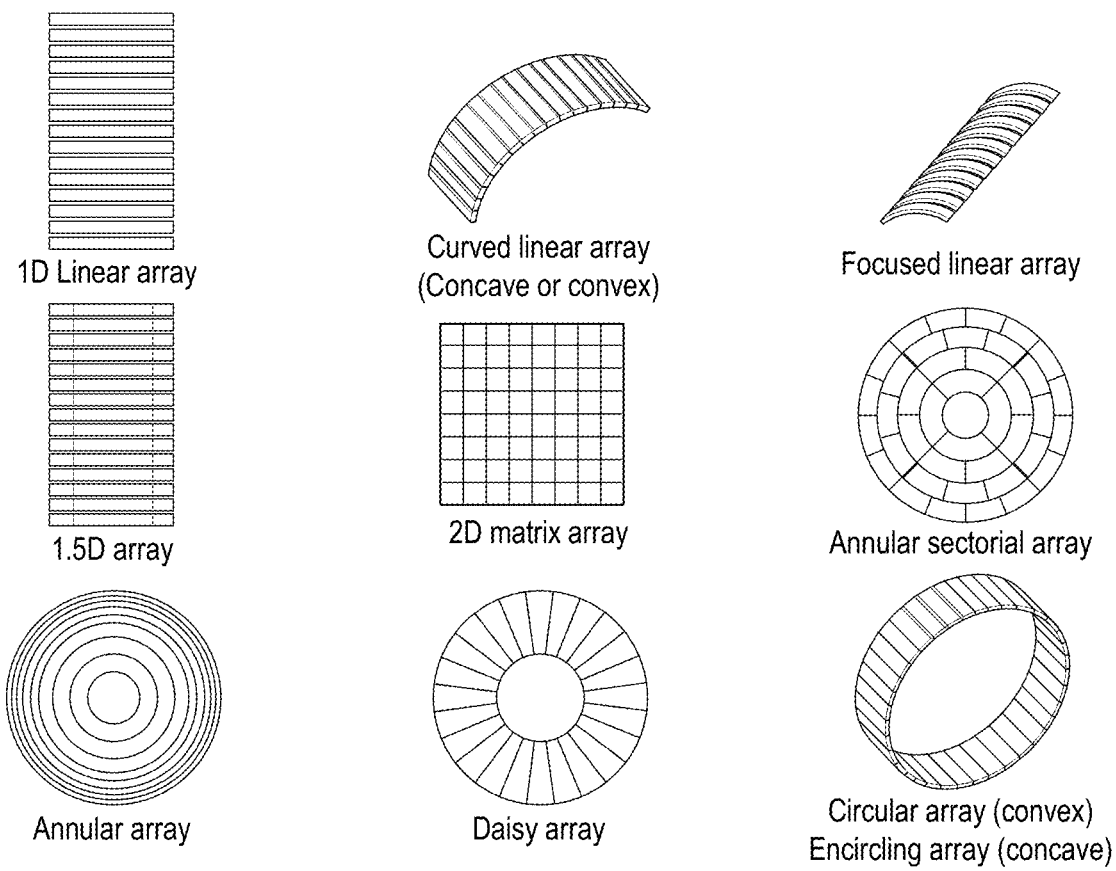
FIG. 5 illustrates generic array types of the transducer of FIG. 4.

Referring to FIGS. 4 and 5, and in one example, the imaging device 14 may include the transducer 60 (FIG. 2), such as an ultrasound transducer 90. The ultrasound transducer 90 employs ultrasound imaging using 2D-phased array transducers. Generally, the ultrasound transducer may include an array of transducer elements, such as a 1D array or a 2D array. As depicted in FIG. 5, generic array types include a 1D limited array, a 1.5D array, an annular array, a curved linear array (concave or convex), a 2D matrix array, a daisy array, a focused linear array, an annular sectorial array, a circular array (convex) or an encircling array (concave). The ultrasound transducer 90 may include any of such generic array types.

The ultrasound transducer 90 pulses and receives from multiple elements in an array. More specifically, elements are pulsed at different times, i.e., with a phase difference. They combine either constructively or destructively to form a single wave front traveling in a desired location. A receiver function of the ultrasound transducer 90 combines the input from multiple elements into a single presentation.

Figure 6:
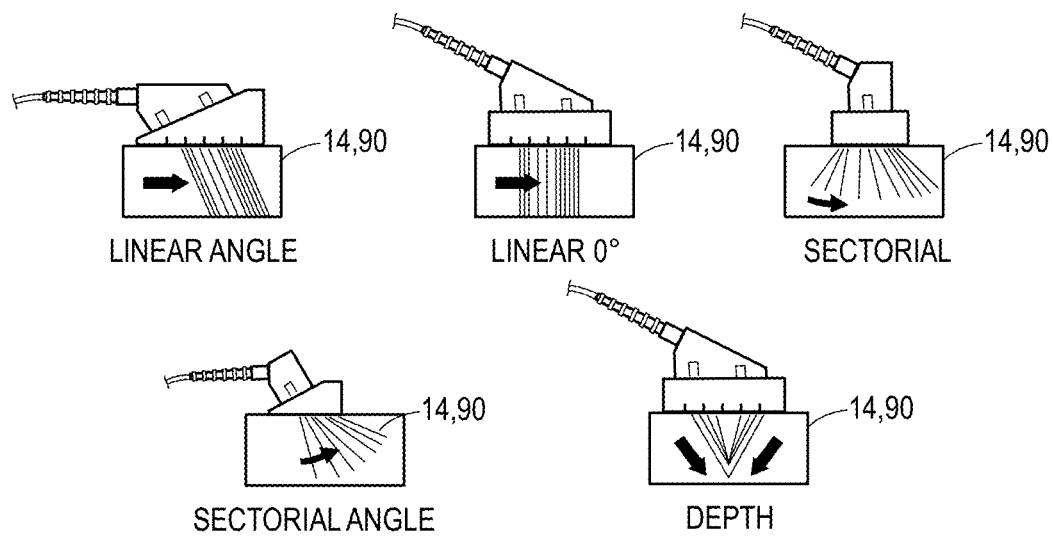
FIG. 6 illustrates the transducer of FIG. 4 with beam steering at different angles.
Figure 7:
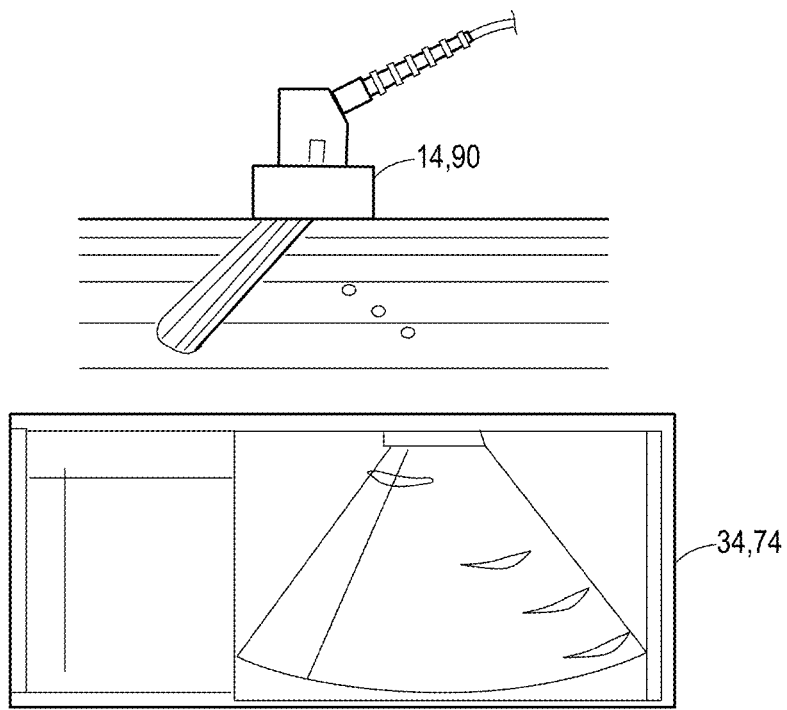
FIG. 7 illustrates an exemplary sectorial scan of the transducer of FIG. 4, the sectional scan a −30 degree to +30 degree sectorial scan.

In addition, phasing technology permits electronic beam shaping and steering. For example, and as depicted in FIG. 6, beam steering of the ultrasound transducer 90 may occur at different angles, such as a linear angle, a linear 0 degrees, sectorial, sectorial angle, and depth. More specifically, and as depicted in FIG. 7, the beam steering of the ultrasound transducer 90 may perform at −30 degree to +30 degree sectorial scan. Images captured during this type of scan may be transmitted and projected on a display, such as the display 34, 74 of one or more of the auto-injection device 12 or the remote data station 26.

The imaging device 14 of the image-guided aspiration and injector system 10 of the present disclosure may be controlled by software implementing pre-programmed values for one or more of a beam angle, focal distance, and/or spot size. In addition, the imaging device 14, such as the ultrasound transducer 90, is capable of multiple-angle inspection, which is ideal for inspection of complex geometries and tests in which part geometry limits access, for example.

Figure 8:
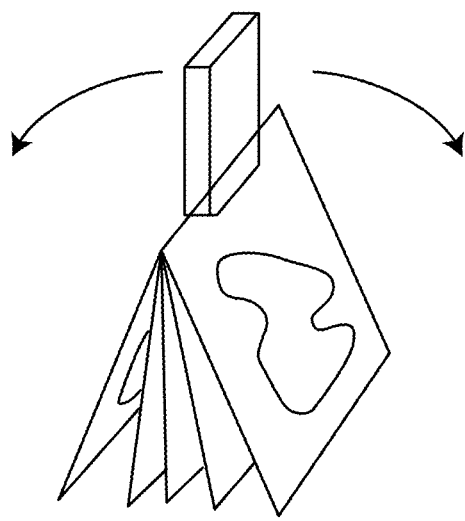
FIG. 8 illustrates an exemplary 3D ultrasound acquisition based on mechanical tilting of an imaging device of the image-guided lumbar puncture aspiration and injector system of FIG. 1.
Figure 9:
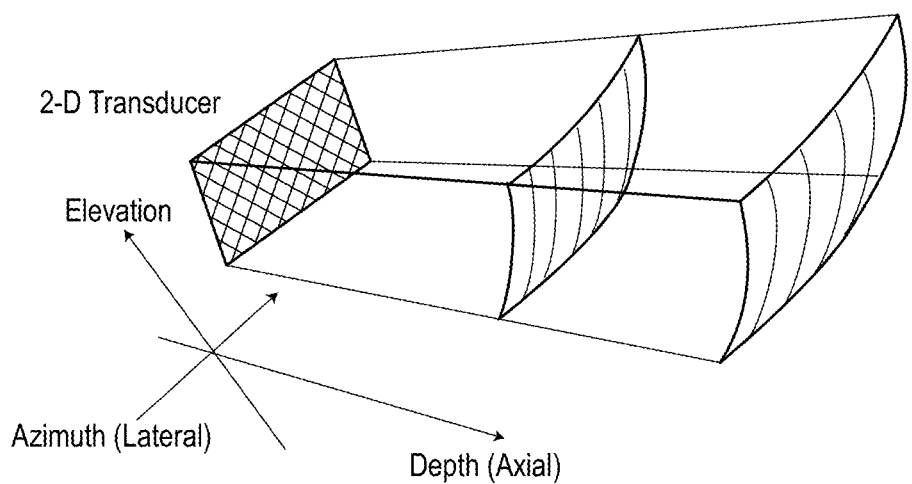
FIG. 9 illustrates an exemplary 3D electronic scanning using a 2D transducer, such as the transducer of FIG. 4.

Generally, the imaging device 14 of the system 10 of the present disclosure is capable of both 2D and 3D imaging. In 2D imaging, a section scan, at an angle θ by means of transmit delays in the array elements is conducted. Different delays for each direction angle of interest are needed. Echoes that return along angle θ will reach the transducer element at different times. The signal received by each array element is combined appropriately. Upon reception, the output signal is the average of appropriately delayed version of the individual transducer output signals. In 3D imaging, there is 3D scanning and 3D scan conversion. In one example, a 1D transducer array is translated, rocked, or rotated to collect a series of 2D images that are later stacked to represent the 3D anatomy, called scanning. FIG. 8 depicts a 3D ultrasound acquisition based on mechanical tilting, and FIG. 9 depicts 3D electronic scanning using a 2D transducer.

Figure 10:
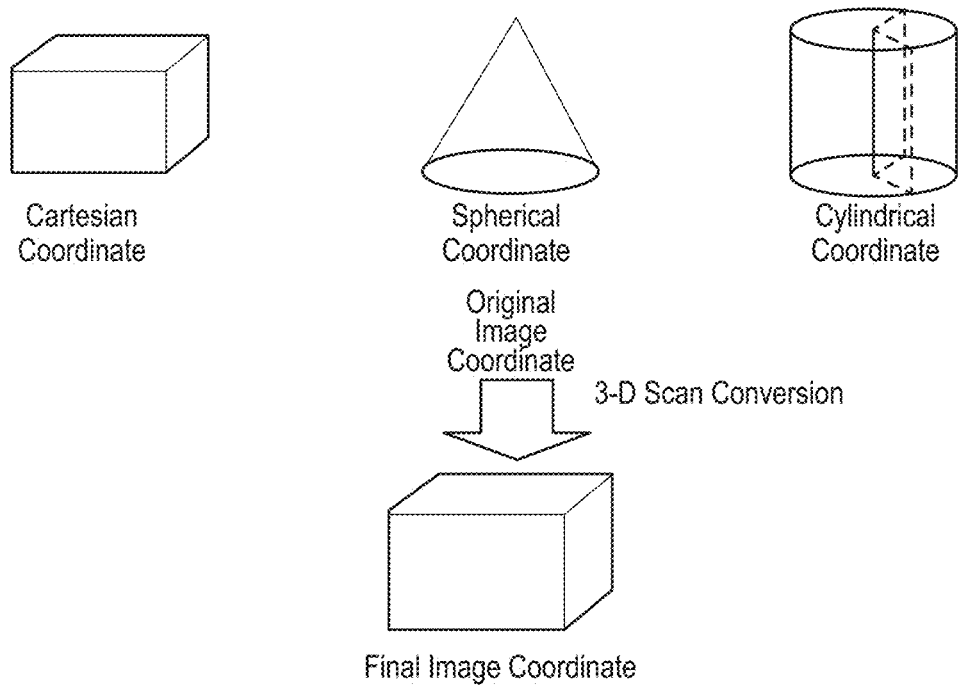
FIG. 10 illustrates an exemplary 3D scan conversion of the system of FIG. 1.

However, 1D array is typically too slow to acquire a 3-D data set in real time. In addition, if the patient 20 or transducer 90 moves during data collection, the 3-D data set can be severely degraded. Such drawbacks are resolved by 2D arrays at least because of their capability to focus ultrasonic beams in two directions. A conversion of the coordinates representing the image is required after scanning, which is called scan conversion, and a 3D image is obtained after further image enhancement techniques. FIG. 10 is an exemplary 3D scan conversion.

Some advantages of using ultrasound technology, like the imaging device 14 of the system 10 of the disclosure, include there is no radiation or heating effect. In addition, phased arrays can reduce data acquisition times by eliminating or reducing the need for mechanical scanning by taking advantage of the ability to perform electronic scanning. Further, the ultrasound technology affords good penetration depth and 2D phased arrays provide 2D beam steering and focusing from a single probe position and, thus, are ideal for imaging complex geometries. Lastly, the phased arrays provide tremendous functionality including real-time 3D imaging and 4D imaging.

Figure 11:
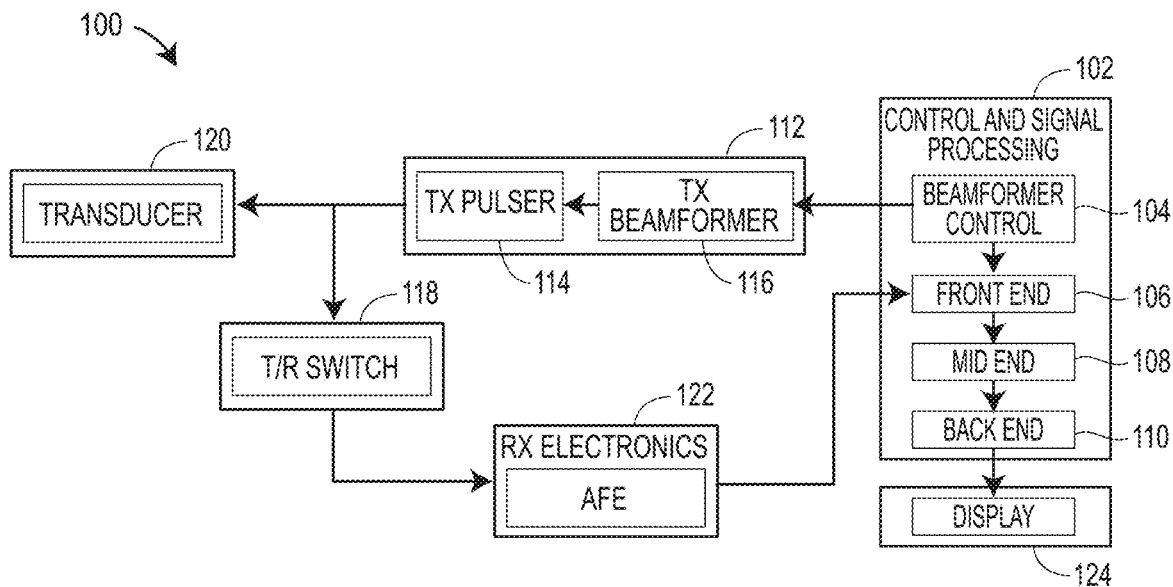
FIG. 11 is a block diagram of an exemplary imaging device, the imaging device including an ultrasound system, of the system of FIG. 1.

Referring now to FIG. 11, an exemplary block diagram of an exemplary ultrasound system 100 that may be used with the image-guided aspiration and injector system 10 of the present disclosure is depicted. The ultrasound system 100 includes a control and signal processing unit 102, which manages beamforming control and the processing of the beamforming control. Specifically, the control and signal processing unit 102 includes a beamformer control unit 104, a front end processing unit 106, a mid end processing unit 108, and a back end processing unit 110, as described more below. The ultrasound system 100 further includes a transmitter 112 having a transmitter pulser 114 and a transmitter beamformer 116, and the transmitter 112 is used for pulsing an ultrasound transducer. Also included is a transmit/receive (T/R) switch 118, an ultrasound transducer 120, which sends out the ultrasound waves, and a receiver 122. The control and signal processing unit 102 is coupled to a display unit 124, which may include one or more of the display 34 of the auto-injection device 12 (FIG. 2), the display 74 of the remote data station 26 (FIG. 2), or another separate display. So configured, and as explained more below, the transmit/receive switch 118 separates the transmitter 112 and the receiver 122, the ultrasound transducer 120 sends out ultrasound waves, the receiver 122 processes the reflected waves from a target, such as the lumbar puncture area 18 of the patient 20, and the display unit 124 renders the ultrasound images detected.

Figure 12:
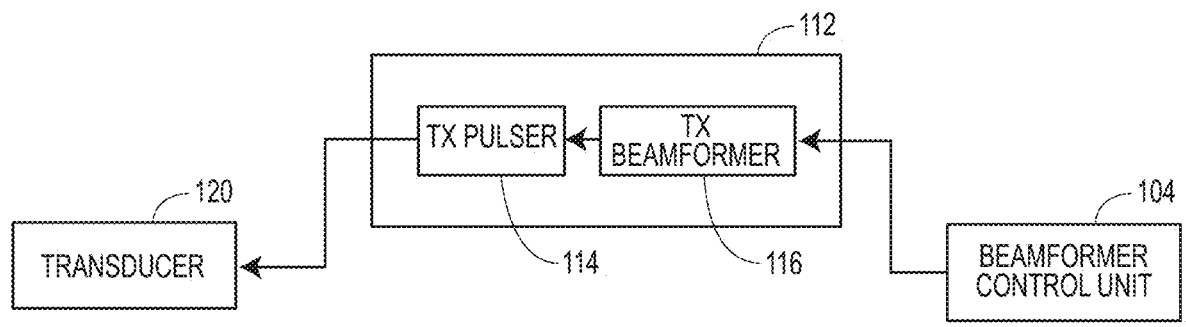
FIG. 12 is a portion of the block diagram of the ultrasound system of FIG. 11, depicting a transmitter coupled to a transducer and a control unit.

More specifically, and referring to FIG. 12, the transmitter 112 circuitry is depicted. As shown, the transmitter 112 is coupled to the beamformer control unit 104 and the transducer 120. The beamformer control unit 104 is responsible for synchronizing the generation of the sound waves and the reflected wave measurements. The beamformer control unit 104 also determines which transducer elements to energize at a given time and the proper time delay value for each element to properly steer the sound waves towards the desired focal point. The transmitter beamformer 116 of the transmitter 112 generates pulses with delays individually controlled for each element group. The transmitter pulser 114 applies high voltage pulses with specified durations and delays to the ultrasound transducer 112.

Figure 13:
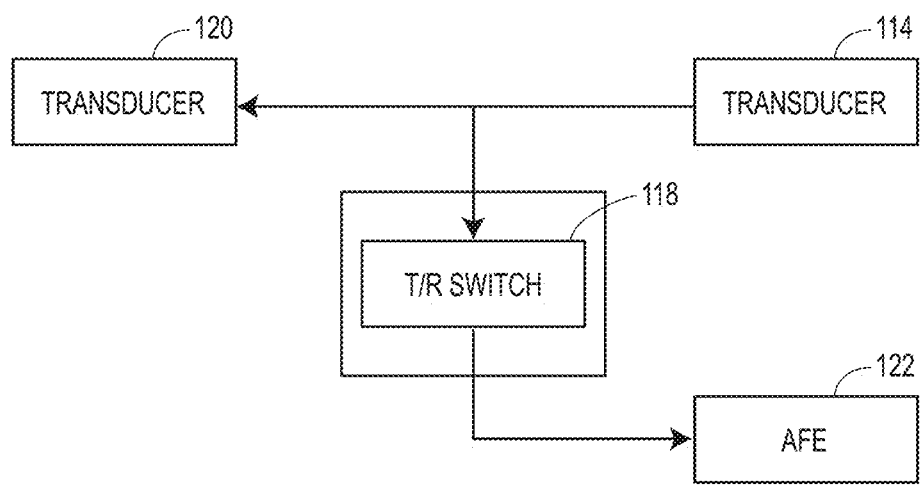
FIG. 13 is another portion of the block diagram of the ultrasound system of FIG. 11, depicting a T/R switch.

Referring now to FIG. 13, the T/R switch 118 is depicted. As shown in FIG. 13, the T/R switch 118 separates the transmitter pulser 114 of the transmitter 112 from the receiver 122 and works as a voltage limiter. The T/R switch is necessary for high-voltage pulse protection of highly sensitive amplifying and digitizing circuits. The transducer 120 converts electromagnetic energy of the pulses from the transmitter pulser 114 into mechanical energy of the ultrasound waves and uses 2D phased arrays, in one example.

Figure 14:
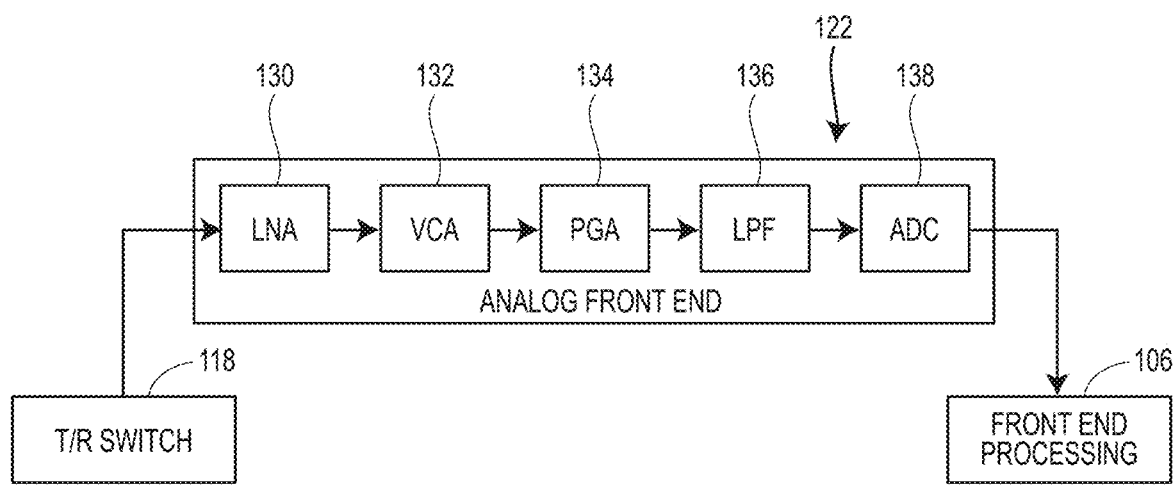
FIG. 14 is an exemplary analog front end for a receiver of the ultrasound system of FIG. 11.

Referring now to FIG. 14, the receiver 122 is depicted. The analog front end of the receiver 122 includes a low-noise amplifier (LNA) 130, voltage controlled attenuator (VCA) 132, programmable gain amplifier (PGA) 134, low-pass filter (LPF) 136 and analog-to-digital converter (ADC) 138. The analog front end for the receiver 122 improves sensitivity and dynamic range, performs time gain compensation to account for signal attenuation, enhances the signal-to-noise ratio (SNR) and converts the signal into the digital domain.

Referring now to FIG. 15A, an exemplary prototype of the ultrasound system 100 of the image-guided aspiration and injection system 10 of present disclosure is depicted. Specifically, the ultrasound system 100 includes the control and processing unit 102, the transmitter 112, the T/R switch 118, the transducer 120, the receiver 122, and the display 124 coupled to the control and processing unit 102. In this example, the control and processing unit 102 is by Texas Instruments model TMDXEVM6678L. In addition, the display 124 is also by Texas Instruments model TMDXEVM8148. Alternatively, other models of both the control and processing unit 102 and the display 124 made by other vendors may be used and still fall within the scope of the present disclosure. In the control and processing unit 102 (FIG. 11), processing occurs in three stages. The front end processing unit 106 performs receive beamforming and is implemented in ASIC, FPGA, DSP or a combination of these components. The mid-end processing unit 108 performs baseband filtering, decimation, envelop detection, and logarithmic compression and produces a gray scale image. The back-end processing unit 110 performs 2D noise reduction, image enhancement, and 3D scan conversion. Other exemplary specifications and options for each of the aforementioned components of the ultrasound system 100 is provided in FIG. 15B.

Figure 16:
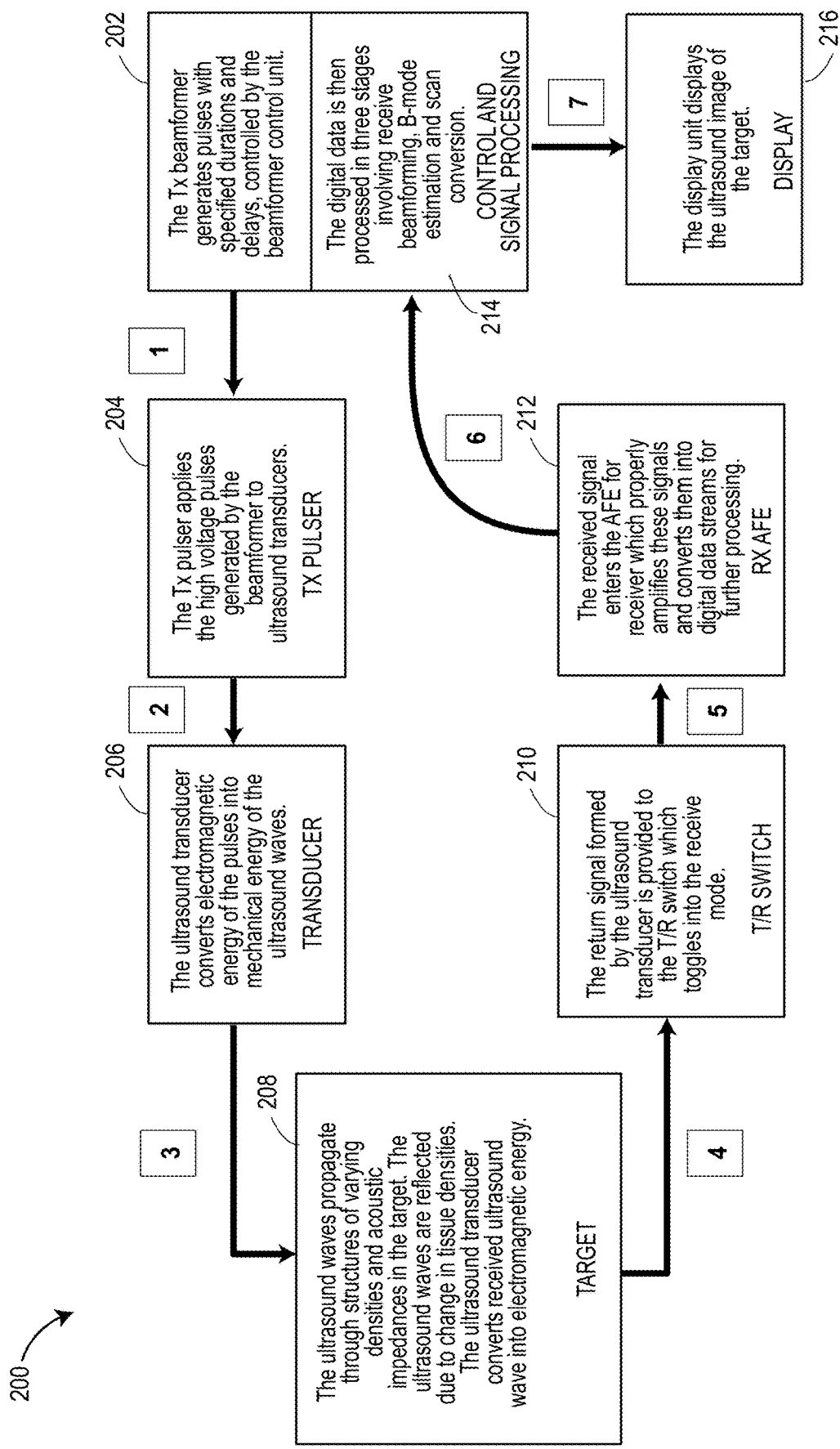
FIG. 16 is a flow chart depicting a method of one aspect of the ultrasound system of the present disclosure.

Referring now to FIG. 16, a flow chart depicting an exemplary method 200 of operating the ultrasound system 100 of the present disclosure is provided. Specifically, at block 202, the transmitter beamformer 116 (FIG. 11) generates pulses with specified durations and delays and is controlled by the beamformer control unit 104 of the control and signal processing unit 102. Next, at block 204, the transmitter pulser 114 applies the high voltage pulses generated by the transmitter beamformer 116 to ultrasound transducers 120 (see, e.g., FIG. 11). At block 206, the ultrasound transducer 120 converts electromagnetic energy of the pulses into mechanical energy of the ultrasound waves. At block 208, the ultrasound waves propagate through structures of varying densities and acoustic impedances in the target, such as the lumbar puncture area 18 of the patient 20 (FIG. 1). The ultrasound waves are reflected due to change in tissue densities. The ultrasound transducer 120 converts received ultrasound wave into electromagnetic energy. At block 210, the return signal formed by the ultrasound transducer 120 is provided to the T/R switch 118 which toggles into the receive mode. At block 212, the received signal enters the receiver 122 AFE, which properly amplifies these signals and converts them into digital data streams for further processing. At block 214, the digital data is then processed in three stages at the control and processing unit 102, the three stages involving receive beamforming, B-mode estimation, and scan conversion. At block 216, the display unit 124 displays the ultrasound image of the target.

Figure 17:
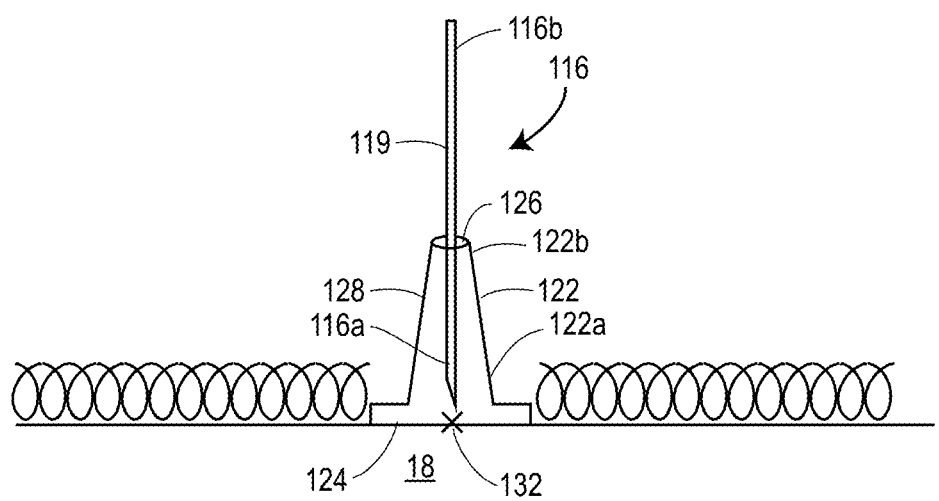
FIG. 17 is a perspective view of another exemplary needle assembly of the image-guided aspiration and injector system of the present disclosure.

Referring now to FIG. 17, a needle assembly 116 according to another aspect of the present disclosure is depicted. The needle assembly 116 is similar to the needle assembly 16 of FIG. 1 in that the needle assembly 116 also includes an inner needle. However, unlike the needle assembly 16 of FIG. 1, the needle assembly 116 does not include an outer needle, but instead includes a needle guide, as explained more below.

More specifically, the needle assembly 116 includes a distal end 116 a adapted to be inserted into the lumbar puncture area 18 of the patient 20 and a proximal end 116 b adapted to be coupled to the at least one syringe 32 of the auto-injection device 12 (FIG. 1). The needle assembly 116 includes a needle 119 and a needle guide 122 through which the needle 119 is inserted. In one example, the needle guide 122 includes a distal end 122 a having a base 124 and a proximal end 122 b having an aperture 126. The needle guide 122 is sterile and at least a portion of the base 124 of the needle guide 122 includes an adhesive adapted to be secured to the lumbar puncture area 18 of the patient 20 before the application of any gel or other ultrasound procedure material. So configured, the needle guide 122 protects a needle insertion site of the lumbar puncture area 18 from any contamination. As depicted, the needle 119, which may be a lumbar puncture needle, is placed through the aperture 126 of the needle guide 122 to access the skin of the patient 20 (FIG. 1) and inserted into a correct location of the lumbar puncture area 18.

Figure 18:
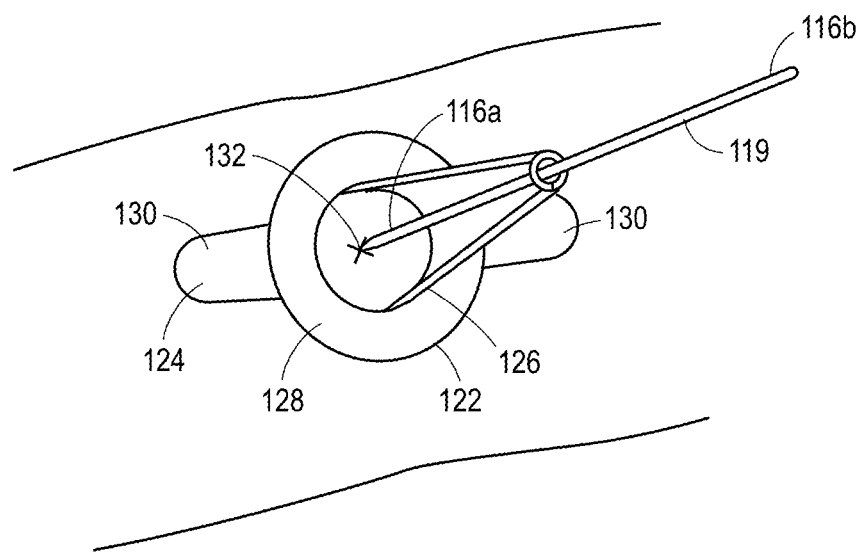
FIG. 18 is a top perspective view of the needle assembly of FIG. 17.

As further depicted in FIGS. 17 and 18, the needle guide 122 further includes a body 128 extending from the base 124. In one example, the body 128 may take the form of a cone-shape, having a first diameter disposed closer to the base 124 and a second diameter smaller than the first diameter disposed closer to the proximal end of the needle 119. As will be appreciated, the body 128 may alternatively take the shape of various other forms and still fall within the scope of the present disclosure. The body 128 includes the aperture 126 and extends upwardly from the base 124 in one example. As depicted in FIG. 18, the base 124 may include two projections 130 outwardly extending from the body 128 of the needle guide 122. In other examples, the base 124 may include a circular member surrounding the entire body 128 of the needle guide 122. In addition, various other shapes of the base 124 may alternatively be used and still fall within the scope of the present disclosure. Further, an entry-point 132 of the needle 119 into the location of the lumbar puncture area 18 may be a center area of one or both of the body 128 of the needle guide 122 or the base 124 of the needle guide 122. So configured, the needle guide 122 directs the needle 119 in the center area.

Referring now to FIGS. 19 and 20, the needle 19, 119 of the needle assemblies 16, 116 of the foregoing are depicted being inserted through the skin 140 and into the dura 142 of the spine 144 of the patient 20. In particular, the distal end 19 a, 119 a of the needles 19, 119 may include a telescoping distal tip 146 for directionality. More specifically, FIG. 19 depicts the telescoping distal tip 146 of the needle 19, 119 disposed within a body 147 of the needle 19, 119. Said another way, the telescoping distal tip 146 is in a retracted position in FIG. 19.

In FIG. 20, the telescoping distal tip 146 is depicted in an extended position, outside of the body 147 of the needle 19, 119. So configured, the distal tip 146 is designed to change direction once outside of the body 147 for an outlet 21, 121 to be one or more of rostral facing, distal facing, or directed toward another specific compartmentalized area in the spine 144.

To operate the image-guided lumbar puncture aspiration and injector system 10 of the present disclosure, the imaging device 14, which may include the ultrasound system 100 described above, is first positioned near and then in contact with the lumbar puncture area 18 of the patient 20. In some examples, the clinician may apply gel to the lumbar puncture area 18 before scanning, but it is not necessary. The imaging device 14 captures data relative to the lumbar puncture area and processes the data to create images relative to the lumbar puncture area 18 of each individual patient 20. Such images may be displayed on the display 34 of the auto-injection device 14 or remotely, for example, such as on the display 28 of the remote data station 26 or another remote device. Upon viewing the images, an accurate location for the lumbar puncture procedure is identified, and the needle assembly 16, 116 is inserted into the accurate location of the lumbar puncture area 18.

Specifically, to insert the telescoping lumbar puncture needle of the needle assembly 16, the outer sheath needle 17 is first used to puncture the skin of the lumbar puncture area 18 of the patient 20. The inner, protected needle 19 is then inserted through the dura of the patient. In the needle assembly 116 of FIGS. 17-20B, the needle guide 122 is first position on a portion of the lumbar puncture area 18. The distal end 116a of the needle 116 is inserted through the hole 126 of the needle guide 122 to puncture the skin of the lumbar puncture area 18 of the patient 20 (e.g., identified by the imaging device 14 as explained above).

The auto-injection device 10 is also positioned proximate the lumbar puncture area 18 (and more particularly the needle assembly 17 or a catheter). The at least one syringe 34 is fluidly connected to the inner needle 19 of the needle assembly 16, such that the at least one syringe 34 is fluidly coupled to the lumbar puncture area 18 within the patient 20. So positioned, the auto-injection device 10 may be then be activated to provide the pre-programmed infusion and/or aspiration.

To activate the device 10, the clinician 22 may, for example, select the pre-programmed infusion and aspiration profile (or the desired infusion and aspiration profile if the device 10 is pre-programmed with multiple profiles) using the display 38. Once the display 38 receives this input, the controller 40 retrieves the selected infusion and aspiration profile from the memory 44 (FIG. 2). The selected infusion and aspiration profile will include an infusion and aspiration protocol in the form of the computing logic, which includes various infusion and aspiration routines, embodied as computer-readable instructions.

Once the controller 40 receives or retrieves the infusion and aspiration profile, the processor 42 carries out the infusion and aspiration protocol stored as computing logic by executing the computer-readable instructions. For example, the infusion and aspiration protocol may include instructions for the processor 42 to expel the fluid 22, 24 from one or both of the syringes 32.

In yet another example, the infusion and aspiration protocol can include instructions for the processor 42 to infuse and/or aspirate the fluid 22, 24 in connection with the at least one physiological parameter and/or the at least one pressure. In other words, the controller 40 may control the infusion and/or aspiration of the syringes 34 using not only the infusion and aspiration protocol but also one or both of the at least one physiological parameter and at least one pressure.

In particular, in one example, the at least one sensor 80 disposed within the housing 30 of the auto-injection device 12 measures at least one pressure and transmits the measured at least one pressure to the controller 40. The controller 40 then compares the measured at least one pressure to a stored, threshold pressure and determines if the measured pressure is greater, less than, or equal to the stored, threshold pressure. If the controller 40 determines that the measured pressure is greater than the stored, threshold pressure, the controller 40 transmits a stop signal to the processor 42, which causes the processor 42 to stop the fluid flow to and/or from the device 10.

It will be appreciated that the system 10 of the present disclosure enables clinicians to detect spinal column through ultrasound imaging, facilitating an easier administration of drug delivery.

The system described herein is suitable for administering fluid composition, such as a pharmaceutical composition comprising one or more therapeutic agents, to a subject. Indeed, the system of the disclosure optionally comprises one or more dosages of a therapeutic agent, such as a therapeutic agent suitable for treating (in whole or in part) a disorder, infection, or injury of the central nervous system or spine. Disorders associated with aspects of the central nervous system or spine include, but are not limited to, spinal muscular atrophy, survival motor neuron deficiency, ankylosing spondylitis, spinal tumors, bipolar disorder, encephalitis, depression, epilepsy, Dravet Syndrome, meningitis, multiple sclerosis, myeopathy, Angelman's Syndrome, CNS lymphoma, Leptomeningeal cancer, Friedreich's Ataxia, hereditary cerebral hemorrhage with amyloidosis-Dutch type (HCHWA-D), cerebral amyloid angiopathy (CAA), amyloid congophilic angiopathy (ACA), and secondary malignant neoplasms (SMN), or neurodegenerative disorders (e.g., Tau protein-related disorders including Alzheimer's disease, Huntington's disease, alpha-synuclei-related disorders including Parkinson's disease, amyotrophic lateral sclerosis (ALS) including superoxide dismutase 1-related ALS, progressive spranuclear palsy, frontotemporal dementia, and Tourette's syndrome. Infections of the CNS include, but are not limited to, viral meningitis, fungal meningitis, epidural infection, viral encephalitis, and neurosyphilis.

Any therapeutic agent may be used in the context of the disclosure. Exemplary therapeutic agents include, e.g., nucleic acids, protein therapeutics, cell therapies, and small molecule therapeutics. Examples of protein therapeutics include antibody-based therapeutics, such as antibodies, antibody fragments, or antibody-like protein products that include binding regions of antibodies (e.g., scFv, diabodies, antibody mimetics, and the like). The antibody-based therapeutic may target, e.g., amyloid plaques, tau proteins, cancer antigens, or abnormal alpha-synuclein. Examples of protein therapeutics also include, but are not limited to, hormones, enzymes (e.g., lysosomal enzymes, such as alpha-L-iduronidase, N-acetylgalactosamine-4-sulfatase, or beta-glucuronidase), growth factors (e.g., fibroblast growth factor (FGF) or neurotrophins or neurotrophic factors, such as glial cell-derived neurotrophic factor (GDNF), brain-derived neurotrophic factor (BDNF), ciliary neurotrophic factor (CNTF), or nerve growth factor (NGF)), blood factors, bone morphogenetic proteins, interferons, interleukins, and thrombolytics. Examples of cell-based therapies include, but are not limited to, stem cell therapeutics and immune cells (including modified immune cells, such as CAR T cells). Suitable small molecule therapeutics include, but are not limited to, analgesics, ion channel blockers, anti-convulsive agents, antibiotics or antiviral agents, anti-inflammatories, anticoagulants, chemotherapeutic, anti-depressants, anti-anxiety agents, steroids, and the like. In various aspects, the therapeutic agent is baclofen, morphine, bupivacaine hydrochloride, clonidine hydrochloride, gabapentin, idursulfase, cytarabine, methotrexate, a corticosteroid, edavarone-conjugate, conotoxin, abomorphine, prednisolone hemisuccinate sodium, carbidopa/levodopa, tetrabenazine, benzodiazepines, such as diazepam and midazolam, alphaxalone or other derivative, cyclophosphamide, idursulfase (Elaprase®), iduronidase (Aldurazyme®), topotecan, buslfan, opmaveloxolone, epicatechin, methylprednisolone, frataxin replacement, reservatrol, nicontinamide, AT-010 (RNA that induces splicing modulation in the mature amyloid precursor protein mRNA), Cerebril™, an anti-Aβ antibody, elenbecestat, a corticosteroid, or nusinersen (Spinraza®), or combinations thereof.

In various aspects, the therapeutic agent is a nucleic acid, including DNA or RNA, which may be single stranded or double stranded and which may be modified or unmodified. Suitable nucleic acid-based therapeutic agents include, but are not limited to, antisense oligonucleotides, ribozymes, miRNA, siRNA, and shRNA. Optionally, the nucleic acid targets a gene selected from the group consisting of APP, MAPT, SOD1, BACE1, CASP3, TGM2, TARDBP, ADRB1, CAMK2A, CBLN1, CDK5R1, GABRA1, MAPK10, NOS1, NPTX2, NRGN, NTS, PDCD2, PDE4D, PENK, SYT1, TTR, FUS, LRDD, CYBA, ATF3, CASP2, HRK, C1QBP, BNIP3, MAPK8, MAPK14, Rac1, GSK3B, P2RX7, TRPM2, PARG, CD38, STEAP4, BMP2, GJA1, TYROBP, CTGF, ANXA2, DUOX1, RTP801, RTP801L, NOX4, NOX1, NOX2 (gp91pho, CYBB), NOX5, DUOX2, NOXO1, NOXO2 (p47phox, NCF1), NOXA1, NOXA2 (p67phox, NCF2), p53 (TP53), HTRA2, KEAP1, SHC1, ZNHIT1, LGALS3, SESN2, SOX9, ASPP1, CTSD, CAPNS1, FAS, FASLG, CAPN1, FADD, CASP1, CASP9, p75NTR, PARK2, HTT (with expanded repeats), NogoA, MAG, OMGP, NgR1, PDE4, BCAN, NCAN, PTPRZ1, TNC, NRP1, NRP2, PLXNA1, PLXNA2, PLXNB1, PLXNC1, TROY, LRRC1, ROCK1, LimK1, LimK2, CFL1, KCNC4, KCNE3, NAT8L, FKBP1A, FKBP4, LRRK2, DYRK1A, AKAP13, UBE2K, WDR33, MYCBP2, SEPHS1, HMGB1, HMGB2, TRPM7, BECN1, THEM4, SLC4A7, MMP9, SLC11A2, ATXN3, ATXN1, ATXN7, PRNP, EFNB3, EPHA4, EFNA5, EPHA7 and EFNB2, such that gene expression or function is modified.

In some embodiments, the therapeutic agent is an oligonucleotide comprising at least one modified nucleotide, optionally a modified nucleotide that reduces binding to cerebral spinal fluid (CSF) proteins. In various embodiments, the modified nucleotide includes a substituent at the 2'-position, such as a 2'-O-2-methoxyethyl ("2'-MOE") group, as shown below, wherein X is O or S:

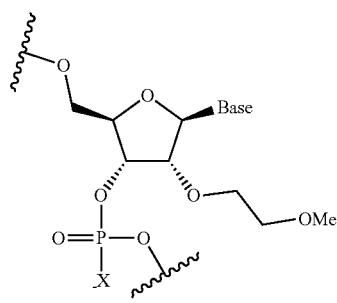

Oligonucleotides comprising a 2'-MOE modification can distribute rapidly in central nervous system tissues. Oligonucleotides comprising such modifications exhibit extended half-lives in CSF and central nervous system tissues, which can result in less frequent dose administration.

In some cases, the modified nucleotide can include a 2',4'-constrained group, such as a constrained 2'-O-ethyl ("cEt") group. In various cases, the cEt group can have S-stereochemistry ("S-cEt"), as shown below, wherein X is O or S.

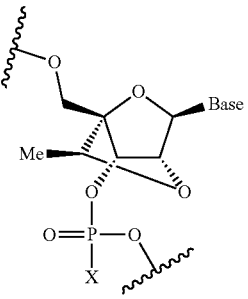

Nucleic acids modified with a constrained ethyl group, such as S-cEt, can exhibit enhanced thermal stability, good potency, and a good therapeutic profile.

Optionally, the nucleic acid encodes a beneficial protein that, e.g., replaces an absent or defective protein, or encodes a cytotoxic protein that achieves a therapeutic effect, such as cancer cell death. Any of the protein-based therapeutics described herein may be delivered to a subject via delivery of a nucleic acid encoding the protein under conditions which allow expression in vivo. For example, in various embodiments, the nucleic acid encodes a neurotrophic factor such as, but not limited to, nerve growth factor (NGF), brain-derived neurotrophic factor (BDNF), neurotrophin-3 (NT-3), neurotrophin-4/5 (NT-4/5), neurotrophin-6 (NT-6), ciliary neurotrophic factor (CNTF), glial cell line-derived neurotrophic factor (GDNF), the fibroblast growth factor family (e.g., FGFs 1-15), leukemia inhibitory factor (LIF), certain members of the insulin-like growth factor family (e.g., IGF-1), a neurturin, persephin, a bone morphogenic protein (BMPs), an immunophilin, a member of the transforming growth factor (TGF) family of growth factors, a neuregulin, epidermal growth factor (EGF), platelet-derived growth factor (PDGF), vascular endothelial growth factor family (e.g. VEGF 165), follistatin, or HifI, or combinations thereof.

In various aspects, the nucleic acid is present in a viral vector. Any viral vector appropriate for delivering a therapeutic agent to a human subject may be used. Examples of viral vectors include, e.g., herpes simplex virus (HSV) vectors, adenovirus (Ad) vectors, parvoviral-based vectors (e.g., adeno-associated viral vectors), chimeric Ad-AAV vectors, and retroviral vectors (including lentiviral vectors, HIV vectors). Any of these gene transfer vectors can be prepared using standard recombinant DNA techniques described in, e.g., Sambrook et al., Molecular Cloning, a Laboratory Manual, 2d edition, Cold Spring Harbor Press, Cold Spring Harbor, N.Y. (1989), and Ausubel et al., Current Protocols in Molecular Biology, Greene Publishing Associates and John Wiley & Sons, New York, N.Y. (1994).

In some embodiments, the viral vector is an AAV vector. AAV vectors used for administration of a therapeutic nucleic acid typically have approximately 96% of the parental genome deleted, such that only the terminal repeats (ITRs), which contain recognition signals for DNA replication and packaging, remain. Delivering the AAV rep protein enables integration of the AAV vector comprising AAV ITRs into a specific region of genome, if desired. AAV vectors are useful for delivering payload to the central nervous system due, at least in part, to their safety profile, long-term gene expression, and ability to infect both dividing and quiescent cells, including neurons. Multiple serotypes of AAV exist and offer varied tissue tropism. Known serotypes include, for example, AAV1, AAV2, AAV3, AAV4, AAV5, AAV6, AAV7, AAV8, AAV9, AAV10 and AAV11. AAV vectors may be engineered to alter the virus native tropism or improve infection by modifying the viral capsid or packaging the genome of one serotype into the capsid of a different serotype. AAV vectors have been used to deliver a number of transgenes to treat a variety of diseases, including ASP to treat Canavan disease; CLN2 to treat Late infantile neuronal ceroid lipofuscinosis; SGSH to treat mucopolysaccharidosis IIIA; NAGLU to treat mucopolysaccharidosis IIIB; ARSA to treat metachromatic leukodystrophy; GAD, AADC, NTN, GDNF, AADC to treat Parkinson's; and NGF to treat Alzheimer's. See, e.g., Hocquemiller et al., Hum Gene Ther., 27(7), 478-496 (2016), hereby incorporated by reference. The genomic sequences of AAV, as well as the sequences of the ITRs, Rep proteins, and capsid subunits are known in the art. See, e.g., International Patent Publications Nos. WO 00/28061, WO 99/61601, WO 98/11244; as well as U.S. Pat. No. 6,156,303, Srivistava et al. (1983) J Virol. 45:555; Chiorini et al (1998) J Virol. 71:6823; Xiao et al (1999) J Virol. 73:3994; Shade et al (1986) J Virol. 58:921; and Gao et al (2002) Proc. Nat. Acad. Sci. USA 99:11854.

It will be appreciated that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. The same reference numbers may be used to describe like or similar parts. Further, while several examples have been disclosed herein, any features from any examples may be combined with or replaced by other features from other examples. Moreover, while several examples have been disclosed herein, changes may be made to the disclosed examples within departing from the scope of the claims.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

We claim:

1. An image-guided aspiration and injector system, comprising:
    an auto-injection device having a housing, at least one syringe carried by the housing and having a fluid and a portion extending outside the housing, and a controller disposed within the housing;
    an imaging device coupled to the auto-injection device and adapted to capture at least one image of a puncture area of a patient;
    a needle assembly coupled to the portion of the at least one syringe of the auto-injection device extending outside the housing and including a needle adapted to be inserted into a dura of the patient; and
    a needle guide having a base and a body extending from the base, the base adapted to be disposed on the puncture area, and the body having an aperture for receiving the needle of the needle assembly,
    wherein, after the needle is inserted into the aperture of the needle guide and into a location of the puncture area identified by the imaging device, the controller is configured to retrieve an infusion and aspiration profile, the infusion and aspiration profile comprising an infusion and aspiration protocol for the at least one syringe, the controller configured to operate the auto-injection device based on the infusion and aspiration protocol, and
    wherein the body of the needle guide is cone-shaped and extends upwardly from the base of the needle guide, the body having a first end including the aperture for receiving the needle and a second end disposed opposite the first end, the second end adjacent to the base, and the base configured to contact a portion of the puncture area and including an adhesive portion adapted to contact the puncture area.

2. The system of claim 1, wherein an entry-point of the needle into the location of the lumbar puncture area is a center area of one or both of the body of the needle guide or the base of the needle guide, the needle guide directing the needle in the center area.

3. The system of claim 1, further comprising at least one sensor disposed in the auto-injection device and configured to measure at least one pressure associated with the patient, wherein the controller is configured to operate the auto-injection device based on the infusion and aspiration protocol and the at least one pressure, and wherein the at least one pressure comprises one or more of an in-line pressure, an infusion pressure, or an aspiration pressure.

4. The system of claim 1, further comprising at least one sensor disposed one or more of in or near the lumbar puncture area location or a location of the patient other than the lumbar puncture area, and the at least one sensor configured to measure at least one physiological parameter for the patient, wherein the controller is configured to operate the auto-injection device based on the infusion and aspiration protocol and the at least one physiological parameter, and wherein the at least one physiological parameter comprises one or more of a cerebrospinal fluid pressure, a cerebrospinal flow rate, an intratumoral pressure, a cerebroventricular pressure, a heart rate, a respiration rate, a protein level, or a biomarker.

5. The system of claim 1, further comprising a display, the display communicatively coupled to the controller and configured to receive an input, wherein the at least one image is rendered on the display and the controller is configured to operate the auto-injection device based in part on the infusion and aspiration protocol and the received input.

6. The system of claim 1, wherein one or more of: (1) the needle comprising a distal end adapted to change direction, such that an outlet of the distal end is one of rostral facing, distal facing, or directed toward a specific compartmentalized area of a spinal column of the patient; or (2) the needle assembly further including a hub having a tactile sensor disposed therein, the tactile sensor adapted to sense when a dura of the patient is pierced.

7. The system of claim 1, wherein the imaging device comprises one or more of: (1) an ultrasound system having one or more of a control and signal processing unit, a transmitter with a transmitter pulser and a transmitter beamformer, a transmit switch, an ultrasound transducer, and a receiver, such that the transmit/receive switch separates the transmitter and the receiver, the ultrasound transducer sends out ultrasound waves, the receiver processes the reflected waves from a target, and a display unit renders the ultrasound images detected; and (2) at least one imaging sensor and a sensor interface, the at least one imaging sensor communicatively coupled to the sensor interface and adapted to capture a profile of a portion of an area in a lumbar puncture area of the patient.

* * * * *